United States Patent [19]

Murata et al.

[11] Patent Number: 5,226,313
[45] Date of Patent: Jul. 13, 1993

[54] BODY FLUID EXCRETION MEASUREMENT APPARATUS FOR MEDICAL APPLICATION

[75] Inventors: Michihiro Murata, Kyoto; Akira Kumada, Kanagawa; Kenji Matsuo, Kanagawa; Chitaka Ochiai, Kanagawa; Shigeo Yamazaki, Kanagawa; Masaaki Kimura, Hyogo; Naoyuki Kohriya, Chiba, all of Japan

[73] Assignees: Murata Mfg. Co., Ltd., Kyoto; Kobayashi Pharmaceutical Co., Ltd., Osaka, both of Japan

[21] Appl. No.: 890,286

[22] Filed: May 26, 1992

Related U.S. Application Data

[63] Continuation of Ser. No. 626,616, Dec. 7, 1990, abandoned.

[30] Foreign Application Priority Data

Dec. 15, 1989 [JP] Japan .................. 1-325504

[51] Int. Cl.⁵ .................. G01F 23/24; G08B 21/00; A61B 5/20
[52] U.S. Cl. .................. 73/149; 73/304 R; 128/771; 340/620
[58] Field of Search .......... 73/149, 304 R; 128/771; 340/618, 620

[56] References Cited

U.S. PATENT DOCUMENTS

| | | | |
|---|---|---|---|
| 3,498,131 | 8/1967 | Rickey | 340/620 |
| 3,781,840 | 12/1973 | Roberts et al. | 340/620 |
| 4,051,431 | 9/1977 | Wurster | 73/861 |
| 4,205,237 | 5/1980 | Miller | 340/620 |
| 4,532,936 | 8/1985 | LeVeen et al. | 128/771 |
| 4,733,560 | 3/1988 | Dam | 340/620 |
| 5,033,300 | 7/1991 | Matsuo et al. | 73/304 |
| 5,097,248 | 3/1992 | Kumada et al. | 73/304 R |
| 5,111,201 | 5/1992 | Matsumura et al. | 73/149 |
| 5,113,143 | 5/1992 | Wei | 73/304 R |
| 5,115,574 | 5/1992 | Givens | 73/304 R |
| 5,138,881 | 8/1992 | Riley et al. | 73/304 R |
| 5,148,708 | 9/1992 | Murata et al. | 73/304 R |

FOREIGN PATENT DOCUMENTS

| | | |
|---|---|---|
| 2330033 | 1/1975 | Fed. Rep. of Germany . |
| 2296839 | 7/1976 | France . |
| 2362369 | 3/1978 | France . |
| 2514498 | 4/1983 | France . |

Primary Examiner—Hezron E. Williams
Assistant Examiner—George M. Dombroske
Attorney, Agent, or Firm—Koda and Androlia

[57] ABSTRACT

A body fluid excretion volume measurement apparatus for medical application. The apparatus stores body fluid excreted from patients in a body fluid storage tank and measures the resistance value with a resistance sensor. The resistance value depends on the shape of the body fluid storage tank, and if the tank is columnar, the resistance value is monotonically increasing with respect to the depth of body fluid. The output of the resistance sensor is processed by a measurement part and electric measurement of the body fluid volume stored in the body fluid storage tank is performed automatically.

16 Claims, 4 Drawing Sheets

BODY FLUID EXCRETION MEASUREMENT APPARATUS FOR MEDICAL APPLICATION

This is a continuation of application Ser. No. 626,616, filed Dec. 7, 1990, now abandoned.

BACKGROUND OF THE INVENTION

1. Field of the Invention

This invention relates to a body fluid excretion measurement apparatus for medical application. The measurement apparatus automatically and continuously records the body fluid excretion (urine and the like) after patients' surgery. This invention relates to improvement of the measurement apparatus.

2. Description of the Related Art

In clinical treatment, especially in surgery, monitoring volume of body fluid excretion of patients is very important for appropriate treatment by doctors. Excretion volume of body fluid (such as blood or urine) is an important datum that reflects the state of patients' recovery. For example, the volume of urine indicates patients' state of recovery after abdominal surgery.

One of conventional measuring methods of body fluid is to store body fluid in a baggy container with a measuring cylinder, and measure the volume manually (Japanese Patent Laid Open No. Sho 46-16464 and Japanese Patent Laid Open No. Sho 57-166147).

Another conventional measuring method is to store body fluid (for example, urine) of a patient in a container, and pours the content into urine container as droplets to measure the volume (Japanese Patent Laid Open No. Sho 57-57524). This method is implemented for practical use.

Further conventional measuring method is to weigh the urine container to obtain the urine volume (Japanese Patent Laid Open No. Sho 60-203237 and Japanese Patent Laid Open No. Sho 63-71008).

All the above conventional methods, however, require a worker to assist the measurement. After the surgery, long term monitoring of the excretion volume is necessary and unit of the measurement can be a whole day. Therefore, it is very difficult to perform the manual measurement.

With the first conventional method, periodic replacement of measuring cylinders is necessary, and increasing the frequency of the replacement enormously increases the load of workers. With the second method, the droplets measuring method, a droplet generation capillary can be blocked with suspension particle in urine, which disables the measurement. With the third method, changes in urine density decrease the accuracy of the measurement. Another problem is that the size of the system tends to become large and expensive. Therefore, automated, continuous body fluid excretion measurement apparatus with simple structure has been desired in the field of clinical treatment.

SUMMARY OF THE INVENTION

The object of the present invention is to provide a simple, inexpensive body fluid excretion measurement apparatus with continuous measurement ability for medical application that does not require human assistance. In achieving the above objective, the present invention proposes a body fluid excretion measurement apparatus for medical application with the following structure.

The apparatus includes a body fluid storage tank. The tank stores body fluid excreted from patients' body. The storage tank has a resistance sensor vertically attached to the inner surface, and the resistance sensor generates electric signals that indicate the resistance value of the resistance sensor based upon the volume of the body fluid stored in the tank.

The apparatus also has a measurement part. The measurement part receives the electric signal generated by the resistance sensor, calculates the resistance value of the resistance sensor based upon the volume of the body fluid stored in the body fluid storage tank, and calculates the volume of the body fluid based on the resistance value.

In the present invention, the volume of the body fluid is measured using electric signals. With this method, necessity of manual assistance decreases considerably. For example, small volume measuring cylinders, conventionally used to increase the accuracy of the measurement, can be replaced with a large tank, which decreases the number of manual replacement of the measuring cylinders. Since droplet generation capillaries are not used, the measurement is not affected by suspension particles in the body fluid. Moreover, lack of weighing machines makes the apparatus smaller and less expensive. Therefore, the present invention enables the implementation of simple, inexpensive, labor saving measuring apparatus that can perform continuous or periodic measurement.

Body fluid measurable with the present apparatus includes urine. Other body fluid is measurable only if its resistance value is measurable. It is preferable that the resistance sensor has more than one resistance bodies. Each resistance body has a specific resistivity and is to be attached parallel to a vertical line on the inner surface of the storage tank. The storage tank may have a sensor substrate, which is fixed on the inner surface of the tank by soft film.

A cable connects the resistance sensor and the measurement part. The cable has a connector on one end and it is removable from a pair of electrodes attached to the resistance sensor. On the other hand, the resistance body also has a pair of output electrodes which are placed parallel to the output electrodes. The short circuit electrode avoid wrong connection of the connectors since it causes a short circuit.

It is better if the relation between the cross sectional area and the depth of the body fluid tank is known, in which case the measurement part can calculate the volume of the body fluid based on the relation between the cross sectional area and the depth of the fluid, and the resistance value of the resistance sensor based upon volume of the body fluid. Furthermore, if the tank has constant cross sectional area at any depth, necessary calculation by the measurement part is further simplified.

The measurement part consists of an impedance testing part, an A/D converter part and a controller/calculator part. The impedance testing part receives, from the resistance sensor, electric signals that indicate the resistance value of the resistance sensor based upon the volume of the body fluid stored in the tank. The A/D converter part receives, from the impedance testing part, analog signals that indicate the volume of the body fluid and converts them into digital values. The controller/calculator part receives, from the A/D converter part, values of the excretion volume and calculates the total volume of the excretion.

In this way, the output of the resistance sensor, which is usually not linear to the volume of the stored body fluid, is converted to an analog signal that is linear to the volume of the body fluid, which makes the manipulation of the measured data much simpler.

The measurement part has a storage part. In the storage part, data that indicate the state of patients' recovery, such as the cumulative volume and transition of the body fluid volume can be stored.

The measurement part also has a timing part. The timing part generates periodic timing signals that indicate the beginning of a new period of cumulative calculation.

The resistance sensors with more than one resistance bodies (and some other resistance sensors) requires driving power. The driving power supplied to the resistance sensor is named a measurement signal. In other words, the measurement signal itself is the driving power of the resistance sensor. A part that generates the measurement signal is named a power supply part hereafter.

If the resistance sensor accepts an alternating current signal (for example, sine wave voltage), the power supply part includes an alternating current signal generator. The alternating current signal generator generates alternating current measurement signals by oscillation caused by direct current voltage from a direct current power supply. The present invention, however, does not depend on (1) the existence of measurement signal, (2) the type of the measurement signal (alternating current or direct current), or (3) the wave form of the measurement signal (sine wave, pulse or the like).

The timing of the measurement with the proposed apparatus can be either continuous or intermittent. If it is intermittent, a means for timing is necessary and the timing signal generated from the timing part can be applied for this purpose using a power controller. The power controller activates the alternating current signal generator according to the timing signal.

If the resistance sensor has transition characteristic, its influence is to be avoided. This can be achieved by delaying the action of the controller/calculation part. By this way excretion volume after the transition without the influence can be obtained.

Using direct current batteries improves the portability of the apparatus. To avoid overflow of body fluid from the tank, the measurement part may have an alarm signal generator. The apparatus watches the volume of the body fluid, and when a predetermined volume of the body fluid has stored in the tank it generates an alarm signal.

The basic advantage of the present invention is to provide simple and labor saving body fluid excretion measurement apparatus for medical application. Therefore, apparatuses with some additional functions like the above, all fall into the technical scope of the present invention.

BRIEF DESCRIPTION OF THE DRAWINGS

The accompanying drawing and its description will facilitate an understanding of the invention. In this drawing, by way of illustration and not of limitation.

DESCRIPTION OF THE PREFERRED EMBODIMENTS

A preferred embodiment in accordance with the present invention is described.

Figure 1:
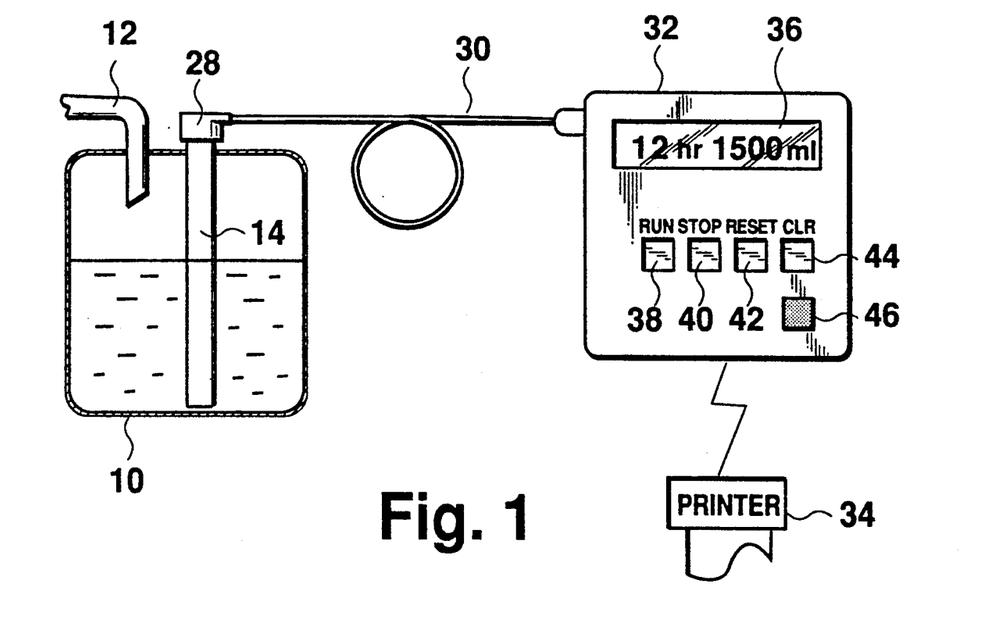
FIG. 1 shows an overall structure of a preferred embodiment in accordance with the present invention, especially the location of a resistance sensor relative to a body fluid tank and the way urine of patients is stored.

FIG. 1 briefly describes an embodiment in which the body fluid excretion volume measurement apparatus for medical application in accordance with the present invention is applied to record urine volume of a post-surgery patients.

A body fluid tank 10 is a circular cylinder or prism made of transparent glass or plastic. The body fluid tank 10 stores urine transferred through a urine pipe 12. The body fluid tank 10 is disposable.

The body fluid tank 10 has constant cross sectional area at any depth. There is a resistance sensor 14 on the inner surface of the storage tank 10. The resistance sensor 14 is fixed on the inner surface of the storage tank 10 and is placed vertically.

Figure 2:
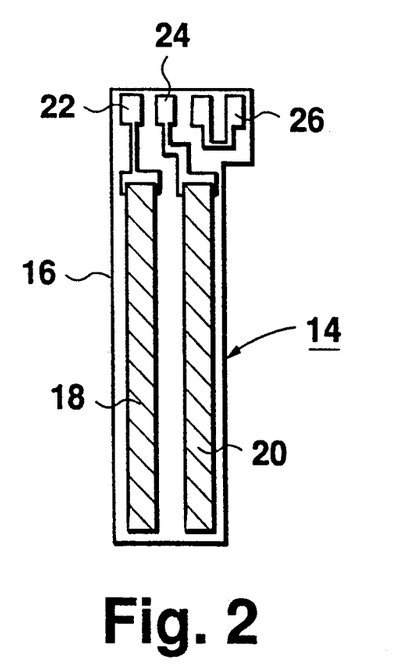
FIG. 2 is a plane view that describes a resistance sensor in the embodiment of FIG. 1, especially parallel alignment of the two resistance bodies, electrodes attached to resistance bodies, and short circuit electrodes.

FIG. 2 is a detailed structural description of the resistance sensor 14. A sensor substrate 16 is a soft film such as polyester film. The sensor substrate 16 is cohesively attached to inner surface of the storage tank 10 with double coated tape or the like.

On the other side of the resistance sensor 14, two resistance bodies are placed. In this embodiment, the resistance bodies are carbon resistance body 18 and 20 that are placed in rows with certain distance. The resistance bodies 18 and 20 are painted or thick-film printed.

Each of the carbon resistance bodies 18 and 20 has electrodes 22 and 24 made of conductive silver paste. When a connector sensor below is attached to the sensor substrate 16, output signals are sent to the electrodes 22 and 24 through connectors, thus, establishing electrical connection among the resistance bodies 18 and 20, the power supply part and the measurement part.

On the sensor substrate 16, there is a short circuit electrode 26 parallel to the electrodes 22 and 24 so that by measuring the resistance value, it is detectable whether the electrodes that are connected to the sensor substrate are 22 and 24, or the short circuit electrode 26. As shown in the FIG. 1, connector 28 will be connected to resistance sensor 14. The resistance sensor 14 will be removed from the connector 28 and disposed after the measurement.

The connector 28 is connected to power supply, measurement, and display part 32 via the cable 30. The power supply, measurement, and display part 32 is driven by a battery, which avoids potential danger caused by commercial alternating power supply and is suitable for medical application. The power supply, measurement, and display part 32 can have peripheral devices. In FIG. 1, a printer 34 is connected to the power supply, measurement, and display part 32.

As clearly shown in FIG. 1, the power supply, measurement, and display part 32 has a display 36 made of liquid crystal or the like. Below the display 36, there are switches 38, 40, 42 and 44 that will be operated by users. The switches 38, 40, 42, and 44 have functions, start, stop, reset and clear, respectively. The alarm buzzer 46 notifies the overflow of the tank 10.

Figure 3:
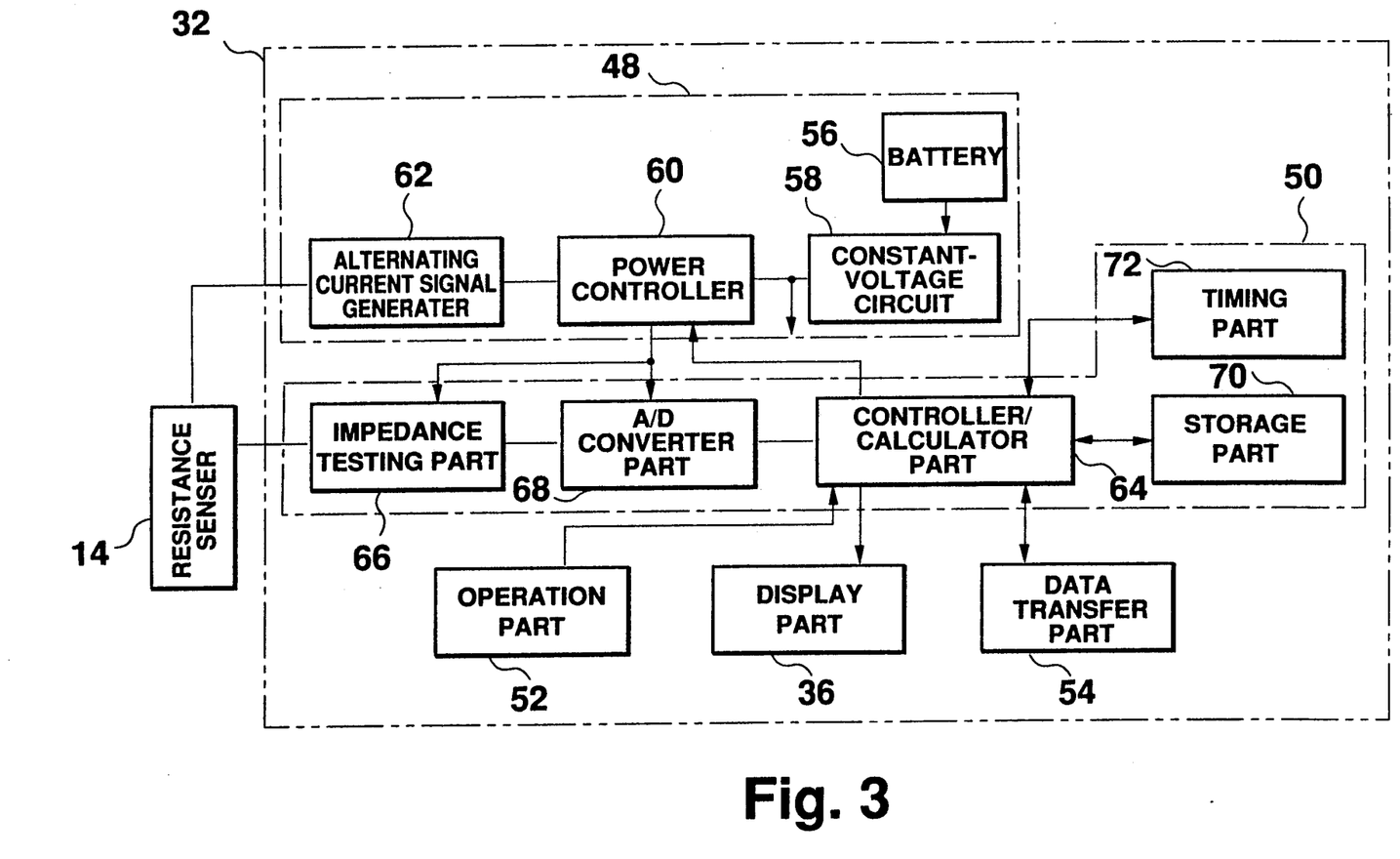
FIG. 3 is a block diagram that describes the structure of a power supply part, a measurement part, and a display part used in the embodiment described in FIG. 1.

FIG. 3 shows a block diagram of the overall structure of the measurement apparatus of the embodiment. In the embodiment the power supply, measurement and display part 32 has a power supply part 48, a measurement part 50, a display part 36, operation part 52 and a data transfer part 54.

The power supply part 48 includes a battery 56. By using a battery 56 as the power supply, the apparatus is portable. The power supply part 48 also includes a constant-voltage circuit 58 which stables the voltage received from the battery, a power controller 60, and an alternating current signal generator 62. The alternating current signal generator 62 receives the direct current voltage from power controller 60, converts it into alternating current voltage, and supply measurement current for the resistance body 18 and 20 of the resistance sensor 14. Here, the measurement current supplied to the resistance sensor 14 can be a pulse signal.

The measurement part 50 includes controller/calculator part with CPU. The measurement part 50 also has an impedance testing part 66 that processes the analog output of the resistance sensor 14 (the depth signal corresponding to the depth of the body fluid in the tank), and sends it to an A/D converter part. The A/D converter part 68 converts the analog signal processed by the impedance testing part into digital signal. The controller/calculator part 64 receives the digital signal and perform necessary calculation.

The controller/calculator part 64 sends the signal to the power controller 60, and controls the current supplied to the resistance sensor 14. The power supply voltage (the output of the constant-voltage circuit) is monitored by the controller/calculator part 64.

The measuring part 50 has a storage part 70 that records the excretion volume calculated by the controller/calculator part 64. The storage part 70 can be a RAM, E$^2$PROM or the like. The measuring part 50 has a timing part 72. With the timing facility, the measurement can be performed intermittently, which increases the life of the battery 56 and enables volume measurement for a long period of time.

The display part 36 has a liquid crystal display or the like. The present invention does not prescribe the detail of structure of the display.

The operation part 52 has keys 38, 40, 42, and 44 and is used to start, stop, reset or clear the record of the apparatus. These keys can be replaced with keyboards or the like.

A data transfer part 54 transfers the data of the body fluid excretion to the outside of the apparatus, for example to a printer 34. RS232C transfer can be used for this purpose.

Detailed description of the measuring principle of the urine excretion volume and the internal state transition of the proposed apparatus in accordance with the present invention follows.

As is well known, body fluid such as urine excreted from patients is electrolyte and, therefore, is an electric conductor. Moreover, resistivity of body fluid reflects the concentration of the body fluid and each body fluid has unique resistivity.

When urine is stored in the body fluid storage tank 10 in FIG. 1, the insulated resistance bodies 18 and 20 placed within a short distance will be electrically connected through the urine. The circuit resistance is known and is very low (approximately 100 Ohm.cm) in the case of urine and the like. If the resistance values of the resistance body 18 and 20 are high enough (for example 100 k Ohm), the resistance of the urine is negligible. Therefore, two resistance bodies 18 and 20 are electrically connected through the urine. At this time, the resistance between the resister bodies 18 and 20 are proportional to the depth of the body fluid. Because the cross sectional area of the body fluid tank is known, the volume of the excreted urine can be calculated by the resistance between the resistance bodies 18 and 20.

Measurement of excretion volume based on the above principle enables automatic, continuous or intermittent measurement. Since the storage tank 10 and the liquid sensor 14 are inexpensive, they can be made of disposable material. This makes the apparatus simple and safe for possible secondary infection.

Figure 4:
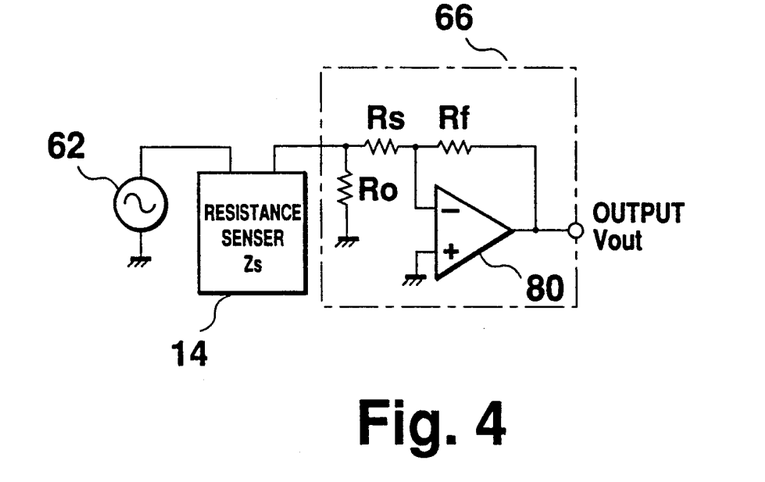
FIG. 4 shows an internal circuit of an impedance testing part used in the embodiment described in FIG. 1.
Figure 5:
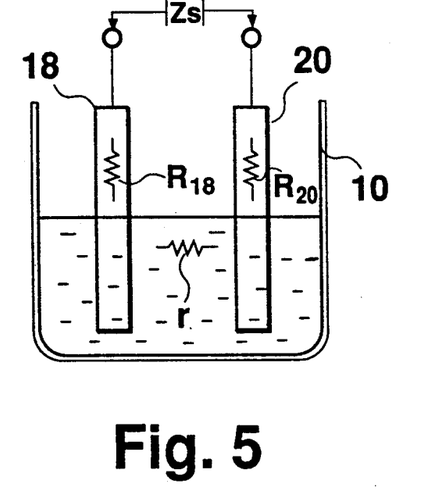
FIG. 5 shows urine stored in a body fluid tank and two resistance bodies described in the embodiment in FIG. 1.
Figure 6:
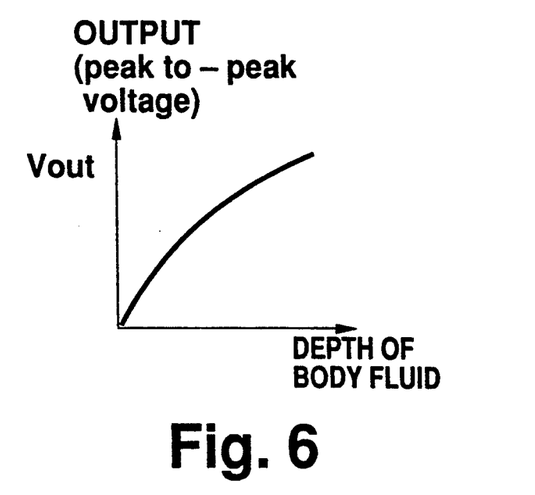
FIG. 6 is a characteristic diagram that describes nonlinear relation between the output of a differential amplifier and the depth of body fluid described in the embodiment in FIG. 1.

Detailed description of the measuring method of the resistance value based on FIGS. 4, 5 and 6 follows. The measurement of the resistance value in the embodiment is performed by supplying alternating current signal to the resistance bodies 18 and 20 of the resistance sensor 14. The alternating current signals can be sine waves with 1 V of amplitude and 10 kHz of frequency. FIG. 4 shows the main structure of the impedance testing part. When the alternating current signal generated from alternating current signal generator is supplied to the resistance sensor 14, the resistance Zs of the resistance sensor 14 (the resistance between the resistance bodies 18 and 20) is obtained as the output voltage Vout of the differential amplifier 80 in the impedance testing part 66. The amplifier 80 includes resistances $R_0$, Rs and Rf as shown in the figure. The output Vout is calculated by the following equation.

$$|Vout| \approx |V_0 Rf/Rs.R_0/(Zs+R_0)|$$

(Here, Zs, $R_0 >> Rs$, and $V_0$ is the output voltage of the alternating current signal generator 62)

FIG. 5 shows an equivalent circuit diagram of the resistance sensor 14 viewed from the electrodes 22 and 24. Because the resistance r of urine is very small, it is negligible compared to the resistance R18 of the resistance bodies 18 and 20. On the other hand, as the depth delta increases, the resistance R18 and R20 of the carbon resistance body 18 and 20 change. FIG. 6 shows the change characteristic of the output Vout of the differential amplifier 80 relative to the depth delta. The characteristic is non-linear but known beforehand. The output Vout is monotone increasing. The output Vout is rectified by the rectification circuit (not shown in the figure) in the impedance testing part 66 and is supplied to the A/D converter part 68. A V/F converter (not shown in the figure) in the A/D converter part 68 generates a rectangle wave with its frequency proportional to the Vout.

The rectangle wave is supplied to, for example, an 8-bit microcomputer in the controller/calculator part 64. The microcomputer has an internal event counter which counts the frequency of the rectangle wave. The counted frequency corresponds to the depth of the urine. The controller/calculator part 64 calculates the volume of the urine excretion using the depth of the urine. The data of storage tank cross sectional area stored in the storage part 70 is used for the calculation. Therefore, with the apparatus of the embodiment, the resistance Zs of the resistance sensor 14, which shows the volume of urine excretion, is measurable at any time.

The measurement part 50 has a timing part 72. The timing part 72 consists of an oscillator, a counter, and a frequency divider, and generates timing information. Using the timing information and the urine excretion volume, the controller/calculator part 64 calculates the total volume of the excretion and incremental volume within a certain period of time. Following the instructions from the operation part 52, the measurement part 50 displays, clears, or transfers the history of the incremental volume. The controller/calculator part 64 also controls the display of measured data on the display part 36. The output from the controller/calculator part 64 is stored in the storage part 70 and is fetched upon request from the operation part 52.

The measured data are transferred from data transfer part 54 to a communication line or a printer 34 and will be used for diagnosis of patients.

The display part 36 consists, for example, of a 7-segment 8-digit LCD, a data latch circuit and a LCD driving circuit. The display part 36 displays the data supplied from controller/calculator part 64. The display part 36 also has alarm facility. The displayed value of the display part 36 in FIG. 1 shows the elapsed time and the total volume of urine excretion.

The alarm facility of the display part 36 is used to prompt the replacement of the storage tank 10, which avoids the overflow of the storage tank 10 and secondary infection. This also avoids the contact of the patient and urine via pipe 12. The alarm is signaled when the depth of the body fluid surpasses a predetermined level and the storage tank 10 will be replaced. For the alarm, the controller/calculator part checks and compares the death of the body fluid with the predetermined value stored in the storage part 70. There is no difficulty in recording the total and incremental volume of the urine after successive replacement of the tank.

In the embodiment, the measurement can be performed without suspension. The measurement, however, can be periodic using the timing signal generated by the timing part 72. For example, the volume of excretion can be measured once an hour according to the timing signal. The power controller 60 and the alternating current signal generator 62 of the power supply part 48, and the impedance testing part 66 and the A/D converter 68 of the measurement part 50, receive the voltage only at periodic time. By restricting the voltage supply in this way, consumption of the battery can be reduced considerably.

Figure 7:
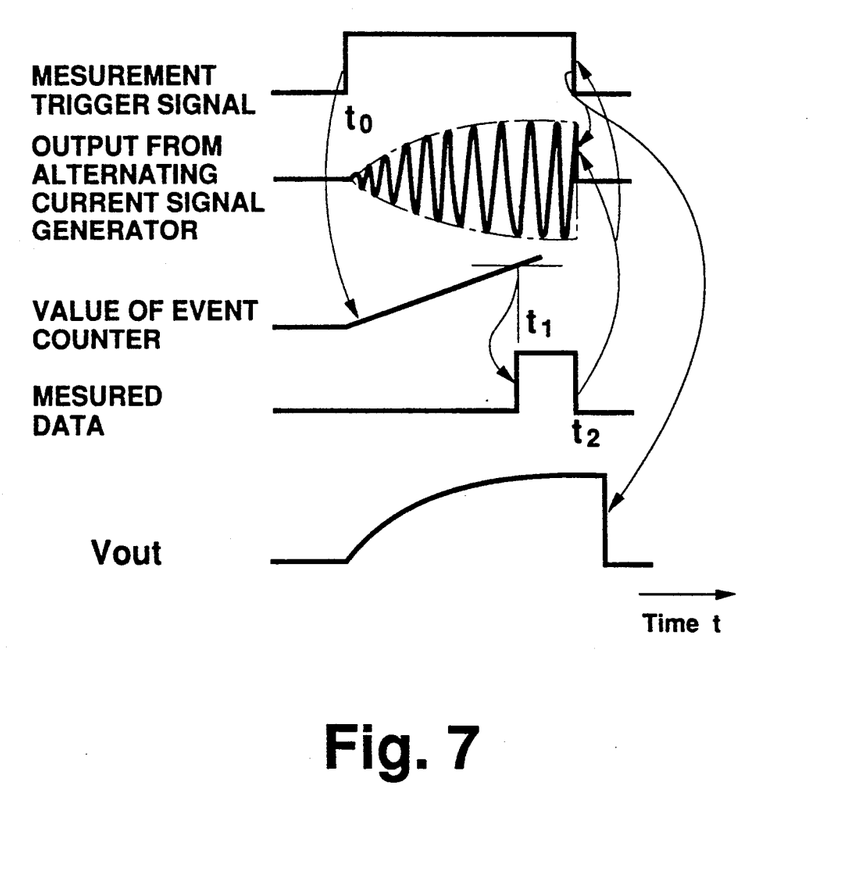
FIG. 7 is a timing diagram in which intermittent invocation of the measurement function is triggered and transition reaction is suppressed by timing control.

Using this type of standby action, the battery is saved in great amount, but this also causes unstable voltage at the early stage of sampling. In the embodiment, the controller/calculator part 64 is equipped with delayed measurement facility at transition period. A measurement trigger signal which the controller/calculator part 64 supplies to the power controller 60 is generated at activation time to as shown in FIG. 7, then the alternating current signal generator 62 oscillates, and the oscillating output is invoked according to the predetermined activation characteristic. By the oscillating output, the output Vout of the impedance testing part 66 is generated. Vout is, then, transformed to a rectangular wave by the A/D converter part. The controller/calculator part 64 counts the wave by the event counter.

After a predetermined period of delay, for example 10 mill value at this moment T1 is sent to the CPU within the controller/calculator part 64 as the measured data. The output Vout has the characteristic shown in FIG. 7, and stable output after the initial transition period is obtained. After the measurement, the measurement trigger signal is reset at time t2 and all the circuits are restored to the standby state. With the embodiment, stable recording of urine excretion volume transition can be enabled, although the measurement signal is generated intermittently.

In the embodiment, an alternating current signal is supplied to the resistance sensor 14, but it is also possible to supply a pulse signal to the resistance sensor and to measure the direct current voltage proportional to the resistance. When using a pulse signal, the volume can be measured by timing the period passed to reach down to a certain voltage, or by measuring the voltage after a certain period of time in the fall of the pulse.

The present invention electronically measures the depth of body fluid in the body fluid tank monitoring the transition of the resistance of the resistance sensor attached to the storage tank, and automatic measurement of body fluid excretion volume without human assistance is enabled. Moreover, the body fluid storage tank and the resistance sensor can be made inexpensively, and these parts that contact with body fluid can be disposable, which remove the possible secondary infection.

What is claimed is:

1. A body fluid excretion volume measurement apparatus for medical application comprising:
    a body fluid storage tank that stores body fluid excreted from a patient's body;
    a resistance sensor that is vertically attached on the inner surface of the storage tank and generates an electric signal that indicates a variation of resistance, the resistance sensor comprising a resistance body and an electrode, and wherein the resistance sensor has a predetermined resistivity and said resistance body comprises more than one resistance means placed parallel to a vertical line;
    a measurement part that receives the electric signal generated by the resistance sensor, calculates a resistance value of the resistance body varied by the volume of the body fluid stored in the body fluid storage tank, and calculates the volume of the body fluid based on the resistance;
    a cable that connects the resistance sensor and the measurement part and transfers from the resistance sensor to the measurement part the electric signal that indicates the variation in resistance of the resistance body based upon the volume of the body fluid stored in the body fluid storage tank; and
    a connector that is attached on one end of the cable and is connected to the resistance sensor;
    the resistance sensor further comprises:
        (a) a pair of output electrodes each of which is electrically connected to a different one of said resistance means, the pair of output electrodes being physically connected to the connector, and the pair of output electrodes indicate the resistance value of the resistance body based on the volume of body fluid stored in the body fluid storage tank; and (b) a pair of short circuit electrodes for obtaining a predetermined connection at said connector placed parallel to the pair of output electrodes; the resistance value of the pair of short circuit electrodes is negligible compared to the resistance value of the resistance means and can be considered as a short circuit.

2. A body fluid excretion volume measurement apparatus for medical application comprising:
a body fluid storage tank that stores body fluid excreted from a patient's body;
a resistance sensor that is vertically attached on the inner surface of the storage tank and generates an electric signal that indicates a variation of the resistance, the resistance sensor having a predetermined resistivity and being composed of a pair of resistance bodies and an electrode;
a measurement part that receives the electric signal generated by the resistance sensor, detects a resistance value of the resistance sensor varied by the body fluid stored in the body fluid storage tank, and calculates the volume of the body fluid based on the resistance;
a cable that connects the resistance sensor and the measurement part and transfers the electric signal that indicates the resistance value of the resistance sensor based upon the volume of the body fluid stored in the body fluid storage tank;
a power supply part that supplies a measurement current to the resistance sensor; and wherein the resistance sensor comprises a sensor substrate that supports the resistance bodies.

3. A body fluid excretion volume measurement apparatus for medical application according to claim 2, wherein the sensor substrate is adhesively attached to the inner surface of the storage tank.

4. A body fluid excretion volume measurement apparatus for medical application according to claim 2, wherein the sensor substrate is a soft film.

5. A body fluid excretion volume measurement apparatus for medical application comprising:
a body fluid storage tank that stores body fluid excreted from a patient's body;
a resistance sensor that is vetically attached on the inner surface of the storage tank and generates an electric signal that indicates a variation of resistance of the resistance sensor, the resistance sensor having a predetermined resistivity and being composed of a pair of resistance bodies and an electrode;
a measurement part that receives the electric signal generator by the resistance sensor, detects a resistance value of the resistance sensor varied by the body fluids stored in the body fluid storage tank, and calculates the volume of body fluid based on the resistance;
a cable that connects the resistance sensor and the measurement part and transfers the electric signal that indicates the resistance value of the resistance sensor based upon the volume of the body fluid stored in the body fluid storage tank; and
a power supply part that supplies a measurement current to the resistance sensor; and
wherein the resistance sensor comprises a pair of output electrodes each of which is electrically connected to a different resistance body, the pair of output electrodes being physically connected to a connector, and the pair of output electrodes indicate the resistance value of the resistance sensor based on the volume of body fluid stored in the body fluid storage tank.

6. A body fluid excretion volume measurement apparatus for medical application according to claim 5, wherein the resistance sensor comprises a pair of short circuit electrodes for obtaining a predetermined connection at said connector placed parallel to the pair of output electrodes, the resistance value of the pair of short circuit electrodes being negligible compared to the resistance value of the resistance bodies and can be considered as a short circuit.

7. A body fluid excretion volume measurement apparatus for medical application comprising:
a body fluid storage tank that stores body fluid excreted from a patient's body;
a resistance sensor that is vertically attached on the inner surface of the storage tank and generates an electric signal that indicates a variation of resistance of the resistance sensor, the resitance sensor composed of a resistance body and an electrode;
a measurement part that receives the electric signal generated by the resistance sensor, detects a resistance value of the resistance sensor varied by the body fluid stored in the body fluid storage tank, and calculates the volume of the body fluid based on the resistance;
a cable that connects the resistance sensor and the measurement part and transfers the electric signal that indicates the resistance value of the resistance sensor based upon the volume of the body fluid stored in the body fluid storage tank; and
a power supply part that supplies a measurement current to the resistance sensor, the power supply part comprising:
  (a) a direct current power supply that generates a fixed voltage; and
  (b) an alternating current generator that oscillates upon receiving the direct current voltage generated by the direct current power supply, and provides the measurement current.

8. A body fluid excretion volume measurement apparatus for medical application according to claim 7, wherein the measurement current is a sine wave form.

9. A body fluid excretion volume measurement apparatus for medical application according to claim 7, wherein the measurement part comprises:
  (a) a timing part that times intervals of measurement and generates a timing signal periodically;
  (b) the power supply part comprises a power controller that activates the alternating current signal generator according to the timing signal; and
  (c) the controller/calculator part starts counting according to the timing signal and outputs excretion volume data in a digital form.

10. A body fluid excretion volume measurement apparatus for medical application according to claim 7, wherein the direct current supply includes a battery.

11. A body fluid excretion volume measurement apparatus for medical application according to claim 7, wherein the measurement part sounds an alarm signal when the volume of the body fluid stored in the body fluid storage tank has surpassed a predetermined level of the storage volume.

12. A body fluid excretion volume measurement apparatus for medical application comprising:
a body fluid storage tank that stores body fluid secreted from a patient's body:

a resistance sensor that is vertically attached on the inner surface of the storage tank and generates an electric signal that indicates a variation of resistance, the resistance sensor comprising a resistance body and an electrode, and wherein the resistance sensor has a predetermined resistivity and said resistance body comprises more than one resistance means placed parallel to a vertical line;

a measurement part that receives the electric signal generated by the resistance sensor, calculates a resistance value of the resistance sensor varied by the volume of the body fluid stored in the body fluid storage tank, and calculates the volume of the body fluid based on the resistance; and wherein the resistance sensor further comprises a sensor substrate that supports the resistance means.

13. The body fluid excretion volume measurement apparatus for medical application according to claim 12 wherein the sensor substrate is adhesively attached to the inner surface of the storage tank.

14. The body fluid excretion volume measurement apparatus for medical application according to claim 12, wherein the sensor substrate is a soft film.

15. A body fluid excretion volume measuring apparatus for medical application comprising:

a body fluid storage tank that stores body fluid excreted from a patient's body;

a resistance sensor that is vertically attached on the inner surface of the storage tank and generates an electric signal that indicates a variation of resistance, the resistance sensor comprising a resistance body and an electrode, and wherein the resistance sensor has a predetermined resistivity and said resistance body comprises more than one resistance means placed parallel to a vertical line;

a measurement part that receives the electric signal generated by the resistance sensor, calculates a resistance value of the resistance sensor varied by the volume of the body fluid stored in the body fluid storage tank, and calculates the volume of the body fluid based on the resistance;

a power supply part that supplies a measurement current to the resistance sensor;

and an alternating current signal generator that oscillates and generates an alternating current measurement signal.

16. A body fluid excretion volume measuring apparatus for medical application comprising:

a body fluid storage tank that stores body fluid excreted from a patient's body;

a resistance sensor that is vertically attached on the inner surface of the storage tank and generates an electric signal that indicates a variation of resistance, the resistance sensor comprising a resistance body and an electrode, and wherein the resistance sensor has a predetermined resistivity and said resistance body comprises more than one resistance means placed parallel to a vertical line;

a measurement part that receives the electric signal generated by the resistance sensor, calculates a resistance value of the resistance sensor varied by the volume of the body fluid stored in the body fluid storage tank, and calculates the volume of the body fluid based on the resistance;

a power supply part that supplies a measurement current to the resistance sensor, the power supply part comprising:

a battery that generates a fixed voltage; and an alternating current signal generator that oscillates upon receiving the direct current voltage generated by the battery and generates an alternating current measurement signal.

* * * * *

UNITED STATES PATENT AND TRADEMARK OFFICE
CERTIFICATE OF CORRECTION

PATENT NO. : 5,226,313
DATED : July 13, 1993
INVENTOR(S) : Michihiro Murata et al It is certified that error appears in the above-identified patent and that said Letters Patent is hereby corrected as shown below:

On the titel page,
Item [73] Assignees: Change "Murata Mfg. Co., Ltd., Kyoto; Kobayashi Pharmaceutical Co., Ltd., Osaka, both of Japan" to --Murata Mfg. Co., Ltd., Kyoto; Kobayashi Pharmaceutical Co., Ltd., Osaka; Emori & Co., Ltd., Fukui, all of Japan--

Signed and Sealed this

Fourteenth Day of June, 1994

*Attest:*

BRUCE LEHMAN

*Attesting Officer*      Commissioner of Patents and Trademarks